US010285680B2

(12) United States Patent
Friedrich et al.

(10) Patent No.: US 10,285,680 B2
(45) Date of Patent: May 14, 2019

(54) RETRACTING TISSUE

(71) Applicant: GLOBUS MEDICAL, INC., Audubon, PA (US)

(72) Inventors: Adam Friedrich, Cinnaminson, NJ (US); Mark Weiman, Coatesville, PA (US); Matthew Bechtel, Norristown, PA (US)

(73) Assignee: Globus Medical, Inc., Audubon, PA (US)

( * ) Notice: Subject to any disclaimer, the term of this patent is extended or adjusted under 35 U.S.C. 154(b) by 471 days.

(21) Appl. No.: 14/183,048

(22) Filed: Feb. 18, 2014

(65) Prior Publication Data

US 2015/0230787 A1  Aug. 20, 2015

(51) Int. Cl.
| *A61B 1/32* | (2006.01) |
| *A61B 17/02* | (2006.01) |
| *A61B 1/06* | (2006.01) |
| *A61B 90/30* | (2016.01) |
| A61B 17/00 | (2006.01) |

(52) U.S. Cl.
CPC ........ *A61B 17/0206* (2013.01); *A61B 1/0676* (2013.01); *A61B 1/32* (2013.01); *A61B 90/30* (2016.02); *A61B 17/0293* (2013.01); *A61B 2017/00473* (2013.01)

(58) Field of Classification Search
CPC ... A61B 17/0206; A61B 17/0293; A61B 1/32; A61B 1/0676; A61B 2017/00473
USPC .................. 606/90; 600/201, 210–219, 226, 600/227–234, 241, 245
See application file for complete search history.

(56) References Cited

U.S. PATENT DOCUMENTS

| 5,400,774 | A | * | 3/1995 | Villalta | A61B 17/0206 600/224 |
| 5,795,291 | A | * | 8/1998 | Koros | A61B 17/02 600/213 |
| 6,139,493 | A | | 10/2000 | Koros | |
| 6,210,323 | B1 | * | 4/2001 | Gilhuly | A61B 17/02 600/208 |
| 7,147,599 | B2 | * | 12/2006 | Phillips | A61B 17/0206 600/219 |
| 8,062,218 | B2 | | 11/2011 | Sebastian et al. | |

(Continued)

FOREIGN PATENT DOCUMENTS

| JP | 2012-507368 A | 3/2012 |
| JP | 2013-509982 A | 3/2013 |

(Continued)

*Primary Examiner* — Zade Coley
*Assistant Examiner* — Jessica Weiss

(57) ABSTRACT

A surgical retractor for retracting body tissue in a therapeutic procedure includes two lateral arms each having a block with an aperture extending transverse to a longitudinal axis of the arm. The distal end of each arm pivotably supports a retractor blade. A transverse extension, forming a retractor core, extends through the aperture and slideably supports a lateral arm at each end. A central arm also pivotably supports a retractor blade, and has an extension on a proximal end that is insertable into an aperture within the core. The lateral and central arms are translatable in connection with the core. The retractor blades can be pivoted by rotating a tool engagement. A rack and pinion, controlled by a pawl, is used to translate the side and central arms.

10 Claims, 7 Drawing Sheets

(56) References Cited

U.S. PATENT DOCUMENTS

| | | | |
|---|---|---|---|
| 8,974,381 B1* | 3/2015 | Lovell | A61B 17/0206 600/232 |
| 9,216,016 B2* | 12/2015 | Fiechter | A61B 17/0206 |
| 9,622,795 B2* | 4/2017 | Reitblat | A61B 17/7077 |
| 9,655,505 B1* | 5/2017 | Gharib | A61B 1/32 |
| 2004/0133077 A1* | 7/2004 | Obenchain | A61B 1/32 600/224 |
| 2004/0193018 A1 | 9/2004 | Thalgott et al. | |
| 2006/0224044 A1 | 10/2006 | Marchek et al. | |
| 2007/0073111 A1 | 3/2007 | Bass | |
| 2008/0188718 A1 | 8/2008 | Spitler et al. | |
| 2008/0249372 A1* | 10/2008 | Reglos | A61B 17/0293 600/205 |
| 2009/0076516 A1* | 3/2009 | Lowry | A61B 17/02 606/90 |
| 2009/0203969 A1 | 8/2009 | Cohen et al. | |
| 2009/0227845 A1 | 9/2009 | Lo | |
| 2010/0081885 A1* | 4/2010 | Wing | A61B 17/0206 600/215 |
| 2010/0113885 A1* | 5/2010 | McBride | A61B 1/32 600/224 |
| 2011/0224496 A1* | 9/2011 | Weiman | A61B 17/0206 600/219 |
| 2011/0301423 A1 | 12/2011 | Koros et al. | |
| 2012/0046527 A1* | 2/2012 | Cianfrani | A61B 17/0206 600/232 |
| 2012/0245431 A1* | 9/2012 | Baudouin | A61B 17/0206 600/213 |
| 2012/0245432 A1 | 9/2012 | Karpowicz et al. | |
| 2012/0303034 A1* | 11/2012 | Woolley | A61B 17/0206 606/90 |
| 2012/0316400 A1 | 12/2012 | Vijayanagar | |
| 2013/0096387 A1 | 4/2013 | Deridder et al. | |
| 2014/0114137 A1* | 4/2014 | Reglos | A61B 17/0293 600/219 |

FOREIGN PATENT DOCUMENTS

| | | |
|---|---|---|
| JP | 2013-537467 A | 10/2013 |
| WO | 02078525 A2 | 10/2002 |
| WO | 2006116336 A2 | 11/2006 |
| WO | 2012026981 A1 | 3/2012 |

* cited by examiner

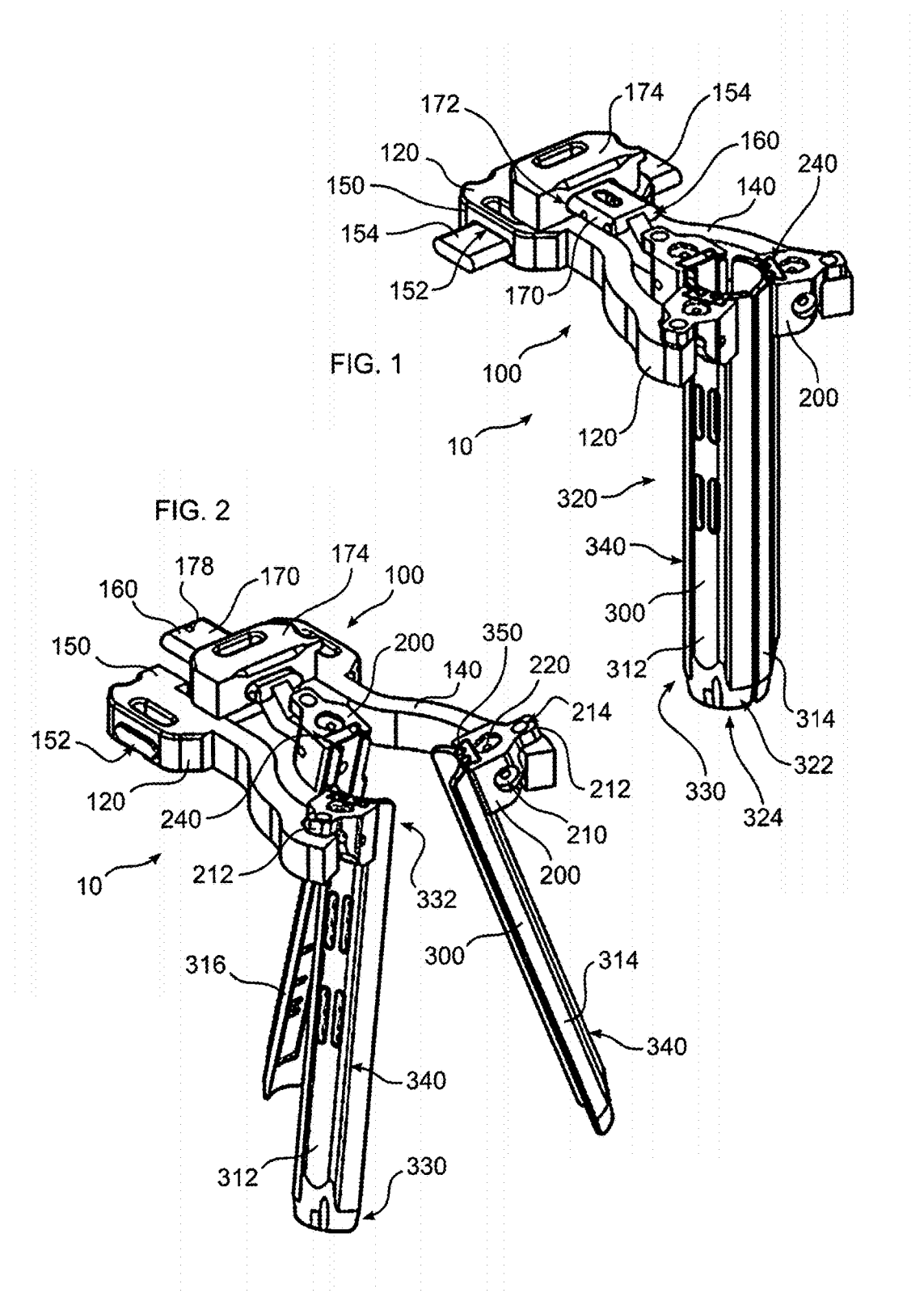

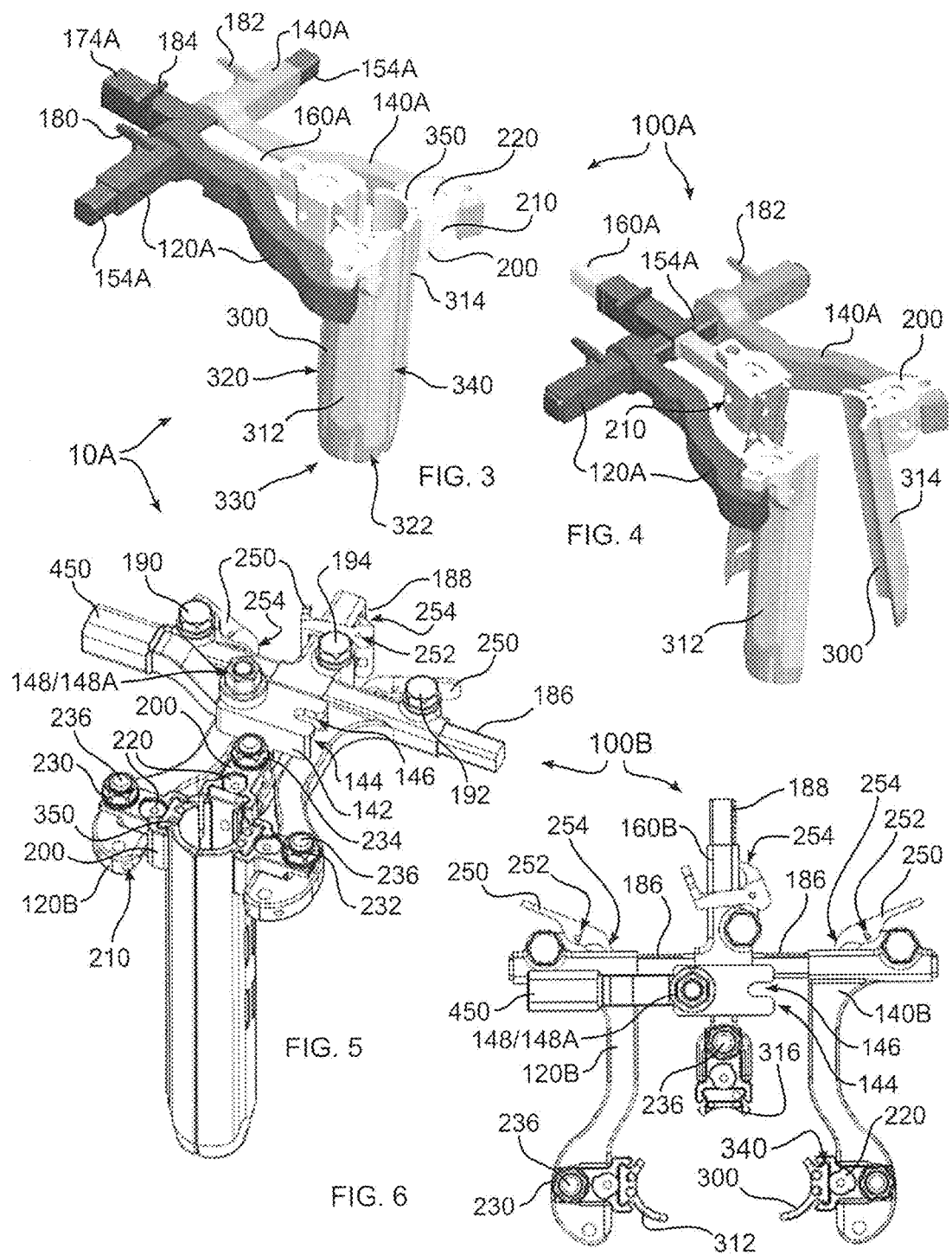

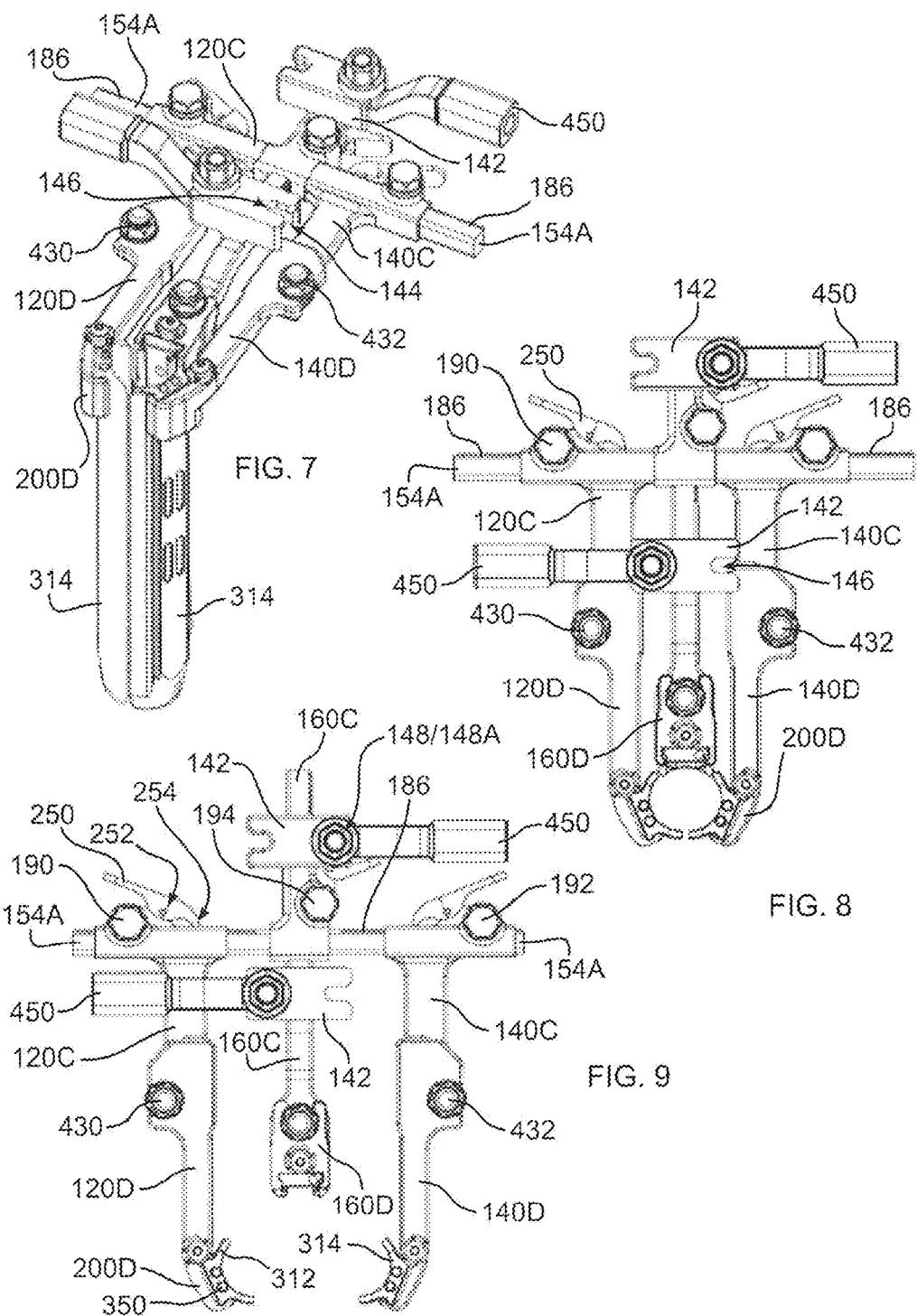

RETRACTING TISSUE

FIELD OF THE INVENTION

The invention relates to a system and method for retracting body tissue during surgery, and more particularly to multi-axis retractors affixed to a base.

BACKGROUND OF THE INVENTION

Retractor systems may be used in a variety of different surgical procedures to provide an opening through which a doctor may access the surgical site. In spinal surgeries, for example, a retractor system may be used to provide the surgeon with access to the patient's spine. The opening created by the retractor system may, for example, enable the doctor to insert surgical instruments into the body or enable visualization of the surgical site using visible light or X-rays.

A retractor system may include a plurality of blades coupled to a retractor frame. In use, the blades may be inserted into an incision and then retracted to displace tissue surrounding the incision along a path to the surgical site. To minimize trauma to the tissue, this tissue displacement should generally be refined and controlled.

SUMMARY OF THE INVENTION

In accordance with an embodiment of the disclosure, a surgical retractor for retracting body tissue in a therapeutic procedure comprises at least one first arm defining proximal and distal ends and a first arm longitudinal axis extending therebetween, the distal end configured to support a retractor blade, the proximal end forming one of an extension or a block having an aperture; at least one second arm defining proximal and distal ends and a second arm longitudinal axis extending therebetween, the distal end configured to support a retractor blade, the proximal end forming one of an extension or a block having an aperture; a core: (a) configured to form a slideable connection each with the at least one first arm and the at least one second arm, (b) the slideable connection with the at least one first arm formed as a block having an aperture when the proximal end of the at least one first arm forms an extension, the slideable connection formed as an extension when the proximal end of the at least one first arm forms a block having an aperture, (c) the slideable connection with the at least one second arm formed as a block having an aperture when the proximal end of the at least one second arm forms an extension, the slideable connection formed as an extension when the proximal end of the at least one second arm forms a block having an aperture, (d) each first arm translatable using the slideable connection independently of translation of at least one second arm, (e) each second arm translatable using the slideable connection independently of translation of at least one first arm, and (f) the distal end of at least one first arm and the distal end of at least one second arm mutually separateable using the slideable connection to thereby separate retractor blades supported upon the at least one first arm and the at least one second arm.

In variations thereof, each first arm is translatable using the slideable connection along an axis transverse to the first longitudinal axis, and each second arm is translatable using the slideable connection along the second longitudinal axis; there are two first arms and one second arm; the two first arms and one second arm formable into a cannula; one or more retractor blades have a tapered end configured to retract tissue that is bone; at least one retractor blade is pivotally mounted to at least one of the at least one first arm and the at least one second arm; pivoting the at least one retractor blade retracts tissue, and separating at least one first arm from at least one second arm retracts tissue; and/or at least one retractor blade is pivoted by rotating a threaded shaft.

In further variations thereof, the retractor further includes at least one blade holder pivotally mounted to at least one of the at least one first arm and the at least one second arm; a blade is connected to each of the at least one blade holder using a dovetail connection; and/or a light source is affixable to at least one retractor blade.

In yet further embodiments thereof, the therapeutic procedure is conducted in a surgical facility having a supporting surface including an extension arm, the retractor further including a mount moveably connected to the core and configured to releasably connect to the extension arm; and/or the mount is moveably connected to the core by a pivot.

In other variations thereof, the slideable connection between at least one of the first and second arms and the core includes a rack and a mating ratcheting pawl, the rack and pawl configured to control relative movement of the at least one first and second arm and the core; the retractor further includes a pinion rotatably secured to one of the at least one first and second arms and the core, the rack associated with the other of the at least one first and second arm, the pinion rotatable to change a relative position of the at least one first and second arm and the core; and/or the retractor further includes at least one of a manually engageable key and a tool engagement connected to the pinion, the key or the tool engagement rotatable to rotate the pinion.

In other embodiments thereof, the retractor further includes a blade holder including a block affixed to at least one of the at least one first and second arms and defining an aperture and an extending flange; a blade retainer having an extension sized and dimensioned to be insertable into the aperture; a threadable set screw connectable between the blade retainer and the extending flange to retain the blade retainer in connection with the block; and/or the retractor further includes a blade holder including a block affixed to at least one of the at least one first and second arms and defining an aperture and an extending flange; a retractor blade having an extension sized and dimensioned to be insertable into the aperture; a threadable set screw connectable between the retractor blade and the extending flange to retain the retractor blade in connection with the block.

In another embodiment of the disclosure, a surgical retractor for retracting body tissue in a therapeutic procedure comprises at least one first arm defining proximal and distal ends and a first arm longitudinal axis extending therebetween, the proximal end defining a first block having a first aperture, the first aperture defining a first aperture longitudinal axis that is transverse to the first arm longitudinal axis, the distal end configured to support a retractor blade; a transverse extension extending through and slideably supporting at least one first block of the at least one first arm; at least one second arm defining proximal and distal ends and a second arm longitudinal axis extending therebetween, the proximal end defining a second extension, the distal end configured to support a retractor blade; and a second block connected to the transverse extension and having a second aperture sized and dimensioned to slideably support at least one second extension, the second aperture defining a second aperture longitudinal axis that is non-parallel with respect to the first aperture longitudinal axis, each second arm translatable in connection with the second block along the second longitudinal axis, each first arm translatable in connection with the transverse extension along the first aperture longitudinal axis, at least one first arm translatable independently of translation of at least one second arm, and at least one second arm translatable independently of translation of at least one first arm.

In a yet further embodiment of the disclosure, a surgical retractor for retracting body tissue in a therapeutic procedure comprises at least one first arm defining proximal and distal ends and a first arm longitudinal axis extending therebetween, the distal end configured to support a retractor blade, the proximal end forming one of an extension or a block having an aperture; at least one second arm defining proximal and distal ends and a second arm longitudinal axis extending therebetween, the distal end configured to support a retractor blade, the proximal end forming one of an extension or a block having an aperture; a core: (a) configured to form a slideable connection each with the at least one first arm and the at least one second arm, (b) the slideable connection with the at least one first arm formed as a block having an aperture when the proximal end of the at least one first arm forms an extension, the slideable connection formed as an extension when the proximal end of the at least one first arm forms a block having an aperture, (c) the slideable connection with the at least one second arm formed as a block having an aperture when the proximal end of the at least one second arm forms an extension, the slideable connection formed as an extension when the proximal end of the at least one second arm forms a block having an aperture, (d) each first arm translatable using the slideable connection along an axis transverse to the first longitudinal axis, at least one first arm translatable independently of translation of at least one second arm, (e) each second arm translatable using the slideable connection along the second longitudinal axis, at least one second arm translatable independently of translation of at least one first arm, and (f) the distal end of at least one first arm and the distal end of at least one second arm mutually separateable using the slideable connection to thereby separate retractor blades supported upon the at least one first arm and the at least one second arm.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 1 depicts a surgical retractor blade holder of the disclosure, the blades held in a configuration conforming to a cannula;

FIG. 2 depicts the retractor of FIG. 1, the blades relatively separated in a manner operative to retract tissue of the body in a therapeutic procedure;

FIG. 3 depicts a retractor of the disclosure, including manually operable adjustment mechanisms for separating blades of the retractor, the blades in a closed configuration;

FIG. 4 depicts the retractor of FIG. 3, the blades in an opened configuration;

FIG. 5 depicts an alternative retractor of the disclosure, including adjustment mechanisms operable with a tool, the blades in a closed configuration;

FIG. 6 depicts the retractor of FIG. 5, the blades in an opened configuration;

FIG. 7 depicts an alternative retractor of the disclosure, including articulated blade holding arms, and a plurality of frame mounts of the disclosure;

FIG. 8 depicts a top view of the retractor of FIG. 7;

FIG. 9 depicts a top view of the retractor of FIG. 7, the blades in an opened position;

DETAILED DESCRIPTION OF THE INVENTION

Figure 10:
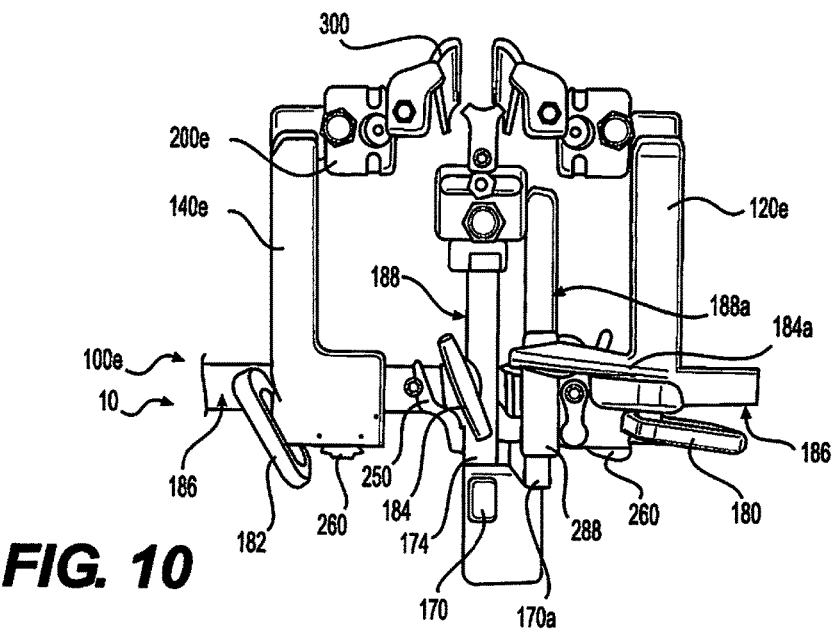
FIG. 10 depicts an alternative embodiment of a retractor of the disclosure, illustrating a thumbwheel operated rack and pinion adjustment mechanism.

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically.

FIGS. 1-2 illustrate, a retractor system 10 that can be used to retract a patient's body tissue in a surgical procedure in accordance with one embodiment of the present disclosure. Retractor system 10 includes a plurality of retractor blades 300, and in this embodiment, a first blade 312, a second blade 314, and a third blade 316. Blades 300 are each coupled to a retractor frame 100, which includes first, second, and third arms 120, 140, and 160, each having a blade holder 200 for holding and positioning a blade 300. In one use of this embodiment, arms 120 and 140 are cranial/caudal, and blade 160 is a posterior blade, although other orientations and uses are contemplated. In an embodiment, each blade may be translated or indexed freely without a requirement to index another blade. In the embodiment shown, arms 120 and 140 are laterally located, and arm 160 is centrally located, although other relative dispositions are contemplated within the disclosure.

Retractor 10 is configured to be adjusted into a desired position, and then releasably fixed to an operating table or other object in the operating theatre, so that a relative position of retractor 10 and a patient can be controlled. Fixation of one or more of retractor 10 can be accomplished using one or more of an operating room (OR) table clamp, a retractor table arm, an arm clamp, and a frame clamp, for example.

Arms 120, 140, and 160 are each linearly translatable to be moveable with respect to each other. More particularly, arms 120 and 140 each include a base 150 having a slot 152, sized to mateably receive and be linearly slideable upon an extension 154. In an embodiment, arms 120 and 140 are mirror images of each other, although this is not necessary in order to carry out all aspects of the disclosure. In the embodiment illustrated in FIGS. 1-2, extension 154 has a flattened profile, thereby preventing unintended rotation of arms 120, 140 with respect to each other, and as described below, with respect to arm 160. Other mechanical forms can be provided for extension 154, including for example a cylinder with a key, to enable a like purpose. In an alternative embodiment of the disclosure, any of arms 120, 140, and 160 can be rotated with respect to other of arms 120, 140, and 160, where extension 154 or 170 (described below) is non-keyed, for example cylindrical.

A threaded set screw (not shown), ratchet (shown in other embodiments herein), or other mechanism can be provided to retain arm 120, 140, 160 in a desired linearly translated position. A rack and pinion configuration, not shown in this embodiment, can be provided, formed between extension 154 providing the rack, and with a pinion rotatably free but displaceably confined within arm 120/140 and engaged with the rack. A locking mechanism, for example a set screw or a ratchet mechanism, can be provided to affix extension 154, 170 at a desired displacement.

Arm 160, in this embodiment, includes an arm extension 170 which translates within a slot 172 within a block 174, block 174 connected to extension 154, for example with screws, or by welding, adhesives, or any other known means. In this manner, an orientation of extension 154 maintains a desired or predetermined orientation with respect to slot 172. Accordingly, as arms 120, 140 are translated upon extension 154, or extension segments 154 that are mutually connected, and as arm 160 is translated within block 174, a relative path of arms 120, 140, and 160 is maintained. Further, each arm 120, 140, 160 is independently translatable with respect to the other arms. In this manner, a medical practitioner can retract tissue in a manner which best suits a therapeutic purpose. Arm extension 170 can be provided with an extension stop 178, to prevent an undesired separation of arm 160 from a remainder of retainer 10.

As can be seen in FIGS. 1-2, arms 120, 140 are sized and dimensioned to fit underneath block 174 when arms 120, 140 are approximated. In this manner, an overall dimension of retractor 10 is minimized, thereby reducing a physical obstruction introduced by retractor 10, and maximizing visualization within the surgical site. Arm 160 can be adjusted and affixed in any translated position as described with respect to arms 120, 160 upon extension 154, however a rack would be formed upon extension 170, and a pinion disposed within block 174.

It should be understood that in this embodiment, as well as other embodiments herein, while arms 120, 140 are configured to form a slot, and translate upon an extension, they could be configured to include extensions which translate within a block, as shown for arm 160. Similarly, arm 160 could form a block which slides upon an extension, as shown for arms 120, 140. In one aspect of the disclosure, the relative configuration of arms 120, 140 and arm 160 provides for an optimal packaging and a reduced physical profile, although various permutations of blocks and extensions as described herein can be provided, which can produce a reduced profile in a similar manner.

As can be seen in FIG. 1, blades 300 are aligned relative to each other to form a tube 320. In an embodiment, tube 320 has a tapered end 322, and can function as a cannula. When retractor 100 is deployed, tube 320 can be formed by inserting blades 300 into an incision or opening in a patient's body, or can be positioned cooperative with other cannulae, to progressively increase a size of an opening in a body sufficient to admit passage of tube 320 with a minimum of disturbance to body tissue. As body tissue relaxes, or when desired, blades 300 can be separated or moved apart by moving arms 120 and 140 relatively apart. The relative extent of movement of arms 120, 140 do not have to be uniform, and at different times, enabling the medical practitioner to control a timing and extent of force exerted upon different portions of body tissue relative to each blade 312, 314. Similarly, blade 316, in connection with arm 160, can be moved before, during, or after movement of either of arms 120, 140, to be closer or further from blades 312, 314.

As blades 312, 314, and 316 are moved relatively apart, a perimeter defined by an exterior surface of blades 312, 314, and 316 is increased, moving body tissue apart, and increasing access to an area within the body. A greater or fewer number of arms 120, 140, and 160 can be provided upon retractor 10 in a like configuration as arms 120, 140, or 160, each configured to move independently of all other arms.

As can be seen in FIG. 2, blades 312, 314, and 316 can be pivoted to be angled or pitched with respect to their respective arms 120, 140, 160. In this manner, distal ends 330 of blades 300 can be further separated, and the perimeter defined by the exterior surface of the blades can be enlarged, without a necessity of increasing an overall profile of retractor 10, or moving arms 120, 140, 160 any further apart.

FIG. 1 depicts retractor 10 in a "closed" or non-retracted configuration, in accordance with one embodiment of the present disclosure. In the closed configuration, blades 312, 314, and 316 are radially disposed around a central bore 324 to form the substantially closed, tube-shaped structure 320. FIG. 2 depicts retractor system 10 in an "open" or retracted configuration, in which blades 312, 314, 316 have been pitched by being pivoted about a pivot 210 connected to a proximal end 332 of a blade 300, and to an arm 120, 140, or 160. In the open configuration, blades 300 no longer form a tube-shaped structure that is substantially closed.

Blades 300 can each be independently pitched or translated, and can be independently pitched or translated with respect to other blades. A stop element 212, in the embodiment shown, a flange, extends from blade holder 200 and contacts arm 120, 140, or 160 at a desired extreme range of pivoting motion of blade holder 200 and associated blade 300. A screw (not shown) can be provided within aperture 214, which may be threaded, the screw configured to bear upon arm 120, 140, or 160 to cause pivoting of blade holder 200, or to function as a stop element operative to change a maximum range of pivoting motion. Alternative embodiments are described with respect to FIGS. 5-6 and 15, elsewhere herein.

Blade holder 200 is provided with a blade engagement profile 240 extending between opposing ends of blade holder 200. Blades 300 are provided with a blade holder profile 340 mateable with blade engagement profile 240, whereby when profiles 240, 340 are mated, blade 300 can be retained upon blade holder 200 and be slideable along a length of blade holder profile 340 so that a penetration of blade 300 with respect to a patient is adjustable. Further, blades 300 can be replaced with blades having a different shape, size, or tissue engaging profile. In one embodiment, blade holder profile 340 and blade engagement profile 240 form a dovetail connection.

Additionally, blades 300 can be inserted after retractor 10 is fixed in a position with respect to a patient, whereby a blade can be slid upwards and away from the patient, and replaced, without a requirement to move retractor 10 or the patient. In this embodiment, blade holder profile extends to a distal end 330 of blade 300, or blade holder profile is configured to no longer provide a mating engagement along one or more portions of a length of blade 300.

Blades 300 are affixed at a desired displacement along the length of blade holder profile 340 by a friction fit between blade holder profile 340 and blade engagement profile 240, or by a set screw or other fastener (not shown) connected to blade holder 200 and contactable with blade 300 or blade holder profile 340.

Blades 300 can be provided with one or more docking pin slots 350 sized and dimensioned to accept a docking pin (not shown), which can be used to secure a blade 300 in a position with respect to body tissue through which a pin is extended, for example into a vertebra. As all blades engaged upon retractor 10 are mutually connected, each docking pin thus inserted contributes to the overall stabilization of retractor 10.

In an embodiment, retractor 10 is configured for an anterior approach to the spine of the patient. In this embodiment, shown in FIGS. 1-2, arms 120, 140 support caudal oriented blades, and arm 160 supports a cranial oriented blade. A range of pitch motion for blades 300 can include 0 degrees (forming tube 320) to 20 degrees, although substantially larger angulation can be provided, for example 30, 40, or 50 degrees, or a greater range of angulation.

In surgical procedures where imaging is to take place, for example X-ray imaging, it is advantageous if at least blades 300 of retractor 10 are at least partially radiolucent, to foster visualization of the imaged area. Accordingly, blades 300 can be fabricated using aluminum, carbon fiber, or polymeric materials, or any other sufficiently strong and radiolucent material, or combination of materials, which is known or hereinafter developed.

With reference to FIGS. 3-6, in an alternative frame embodiment 100A of the disclosure, retractor 10A includes elements similar to those of the embodiment of FIGS. 1-2, and bears similar reference numbers. In FIGS. 3-4, arms 120A, 140A, and 160A support blades 300 in a manner similar to arms 120, 140, and 160 of FIGS. 1-2, but arms 120A, 140A form square or rectangular channels which translate upon extensions 154A. Similarly, arm 160A translates within a rectangular channel forming block 174A. Keys 180, 182, and 184 are positioned to be rotated by a medical practitioner while retractor 10A is deployed, thereby translating arm 120A, 140A, or 160A. With additional reference to FIGS. 5-6 and 11, each of keys 180, 182, and 184 are connected to a pinion (not shown) rotatably fixed to arm 120A, 140A for keys 180, 182, and to block 174A for key 184. A toothed rack 186 is formed upon a side surface of each extension 154A, and a similar toothed rack 188 is formed upon a side surface of arm 160. In this manner, rotation of key 180, 182, or 184 causes a corresponding translational movement of arm 120A, 140A, and 160A, respectively. In FIG. 4, keys 180 and 182 have been rotated to separate arms 120A, 140A, and key 184 has been rotated to retract arm 160A.

In FIGS. 5-6, as can be seen in frame embodiment 100B, in place of keys 180, 182, and 184, tool engagements 190, 192, 194 are connected to rotatably fixed pinions mateable with racks 186, 188. Tool engagements 190, 192, and 194 are engageable by a driving tool, such as a hex or allen head driver. Accordingly, a driving tool (not shown) can be rotated by a hand of a medical practitioner, or by an electrical or computer controlled actuator, to adjust a position of arms 120B, 140B, or 160B, and thereby change a position of one or more blades 300, including for example blades 312, 314, or 316. It should be understood that either a key 180 configuration, or a tool engagement 190 configuration, as shown in FIGS. 3-6, can be provided in the embodiment of FIGS. 1-2.

With further reference to FIGS. 5-6, a blade pitch tool engagement 230, 232, 234 is provided, rotatable using a tool as described with respect to tool engagements 190, 192, and 194, and operative thereby to change a pitch of a blade 300 attached to blade holder 200.

More particularly, in one configuration, blade holder 200 is pivotally mounted at pivot 210, and blade pitch tool engagement 230, 232, and 234 are each rotatably retained upon their respective blade holder 200. Threaded shaft 236 is keyed to prevent rotation, but is axially displaceable by rotation of blade pitch tool engagement 230, 232, 234. As a result, shaft 236 can be caused to bear against arm 120B, 140B, 160B to cause rotation of blade holder 200 about pivot 210, and to thereby change an angle of blade 300. In another embodiment, blade pitch tool engagement 230, 232, 234 is affixed to shaft 236, and shaft 236 is threadably received within blade holder 200. Thus, as blade pitch tool engagement 230, 232, 234 is rotated, shaft 236 bears against its respective arm 120B, 140B, 160B. In a variation of this embodiment, shaft 236 is threadably received within arm 120B, 140B, 160B. Other variations, including a threaded blade holder 200, can be provided. In any of the foregoing embodiments, a biasing element (not shown) can be provided to bias blade holder 200 in a closed or pitched position, where a position of blade holder 200 is not positive controlled in each direction of rotation about pivot 210. It should be noted that in one embodiment, the blade holder 200 may be positively controlled in each direction about the pivot 210. While not shown for all embodiments, it should be understood that the foregoing blade holder pitch mechanism described for FIGS. 3-6 can be provided for other embodiments herein.

Figure 15:
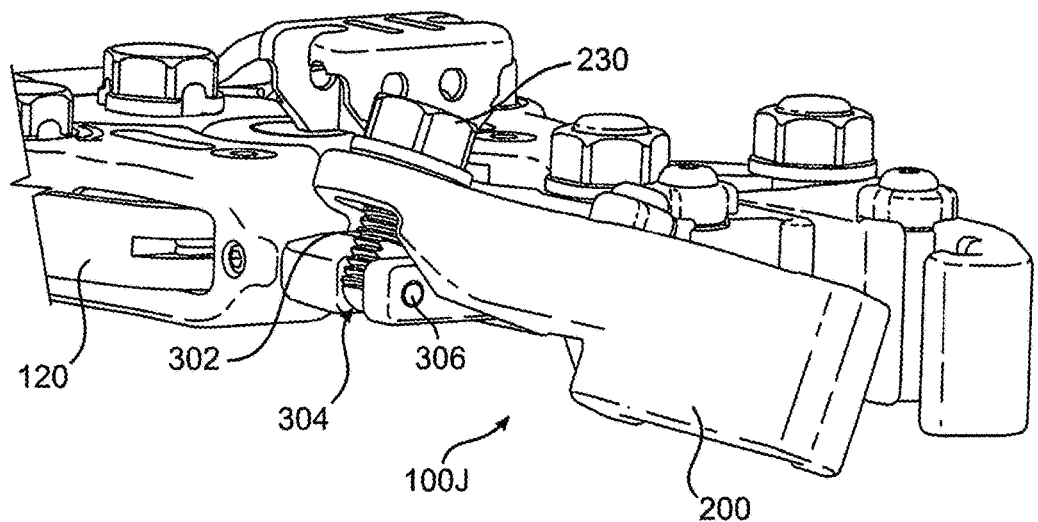
FIG. 15 depicts an alternative blade pitch mechanism of the disclosure.

FIG. 15 illustrates an alternative embodiment, including frame 100J, for controlling blade pitch. More particularly, changing an angulation or pitch of blade holder 200 is accomplished by rotating blade pitch tool engagement 230, which has an attached threaded shaft 302, within a corresponding threaded receiver 304 pivotally connected to blade holder at pin 306.

Blade pitch tool engagement 230, 232, or 234 can be engaged with a tool, for example an allen or hex wrench, or may be provided with a knurled nut or manually engageable key. In this configuration, blade 300 can be pitched at a theoretically infinite range of angles. Other embodiments can be provided wherein blade 300 can be pitched at discrete stop points. A tool thus engaged can also be used to manipulate all or portions of retractor 10, or a separate tool engagement can be provided upon retractor 10 to enable manipulation of other components of retractor 10 described herein.

With further reference to FIGS. 5-6, a ratcheting pawl 250 can be provided, pivotable about pawl pivot 252, a pawl 250 provided for any or all actuators having a toothed rack, including arms 120B, 140B, and 160B, and all other embodiments herein upon which a rack is formed. A pawl tooth 254 has a sloped surface configured to allow rack 186, 188 to pass in one direction, but not an opposite direction. In the embodiment shown, pawl 250 enables arms 120B, 140B, and 160B to move apart, relative to each other. This operates to maintain tissue retracted during a therapeutic procedure. When the procedure is complete, or it is desired to otherwise remove retractor 10, pawl 250 can be rotated about pivot 252 to disengage pawl tooth 254 from rack 186, 188, whereupon key 180, 182, and 184, or tool engagement 190, 192, or 194 can be rotated to change a position of its associated arm.

In an alternative embodiment, pawl 250 does not include a sloped surface at pawl tooth 254, and accordingly the pawl must be retracted from contact with rack 186 or 188 to enable movement of the associated arm.

FIGS. 5-6 further illustrate a frame mount 142, which enables frame 100 (or frame 100A, 100B, and other frame embodiments herein) of retractor 10 to be mounted to a table or other supporting structure with a single mounting point. A support coupling 450 is affixed to the supporting structure with a rod (not shown) threadably or otherwise securable within an end of coupling 450. Coupling 450 includes a threaded rod 148 and nut 148A extending from an end portion. Coupling 450 is inserted into chamber 144 of frame mount 142, and the attached threaded rod is passed into notch 146. Nut 148A is tightened to secure coupling 450 to frame mount 142, and thereby securing retractor 10 to a supporting structure. The frame mount 142 illustrated includes two notches 146, thereby enabling a support coupling to be connected to either side, or to both sides, of frame mount 142. Two or more frame mounts 142 can be provided, as illustrated in FIGS. 7-9, providing multiple or alternative mounting points for retractor 10. In FIGS. 7-9, it may be seen that arm extension 160D is connected to arm 160C using a similar attachment mechanism.

With further reference to FIGS. 5-6, a cam latch 220 is rotatably retained upon blade holder 200, and is oriented to engage a slot (not shown) within blade 300. In this manner, blade 300 is releasably retained upon blade holder 200, and is prevented from sliding within blade holder profile 340. Alternatively, cam latch 220 can overlap a protrusion (not shown) formed upon blade 300.

The embodiment of FIGS. 7-9 is analogous to the embodiment of FIGS. 1-2 and 3-6, however arms 120C, 140C include arm extensions 120D, 140D, and arm couplings 430 and 432. In one embodiment, rotation of coupling blade pitch tool engagements 430, 432 are configured to change a pitch of blades 312, 314 in a similar manner as described with respect to blade pitch tool engagements 230, 232. However, by positioning the corresponding pitch actuating components proximal with respect to blades 300, less structure is imposed upon the target therapy site, improving visualization and manipulation within the target zone. Blade holders 200D are configured to be compact, particularly as articulation does not need to be supported near a blade 300 attachment.

Figure 16:
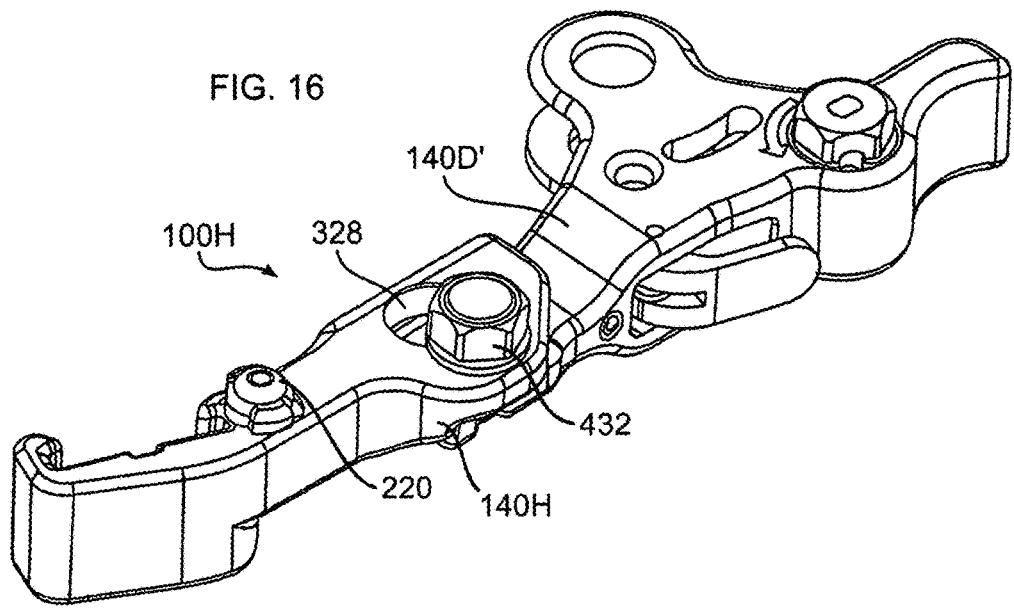
FIG. 16 depicts an articulated blade holding arm in accordance with the disclosure.

In an alternative embodiment, engagements 430, 432 are coupled to pinions which rotate upon a rack formed in arm 120C or 140C. Thus, rotation of engagements 430, 432 extend or retract arm extensions 120D, 140D. Alternatively, engagements 430, 432 enable articulation of arm extensions 120D, 140D when rotated in one embodiment, and when loosed and manipulated in another embodiment. Articulation can be carried out by pivoting arm extension 120D, 140D about a pivot defined by engagement 430, 432, respectively. In a yet further embodiment, couplings 430, 432 enable rapid replacement of arm extensions 120D, 140D. In a yet further embodiment, engagements 430, 432 are connected to threaded shafts (not shown), which lie within elongated slots 328. In this manner, arm extensions 120D, 140D can be displaced laterally with respect to arms 120C, 140C. In a variation of this embodiment, arm extensions 120D, 140D can be pivoted after lateral displacement within elongated slots 328. An embodiment frame 100H having elongated slots 328 disposed within arm 140D' and arm extension 140H is shown in FIG. 16.

With reference to FIG. 10, an embodiment of a retractor 10 of the disclosure includes a frame 100E combining various elements described elsewhere herein, as indicated, and further includes thumbwheels 260 for changing a relative offset of arms 120E, 140E. In an embodiment, a pinion (not shown) rotatably connected to thumbwheel 260 engages rack 186 to cause movement of arm 120E or 140E relative to extension 154E.

As can further be seen in FIG. 10, an additional moveable extension 170A is provided with a rack 188A and pinion (not shown) controllable, in this example, with a key 184A. A mounting block 288 is connected to block 174, whereby extension 170A can be moved independently of extension 170, and arm 188. In an embodiment, extension 170A is connected to a supporting structure, frame 100E moveable with rotation of key 184A.

Figure 11:
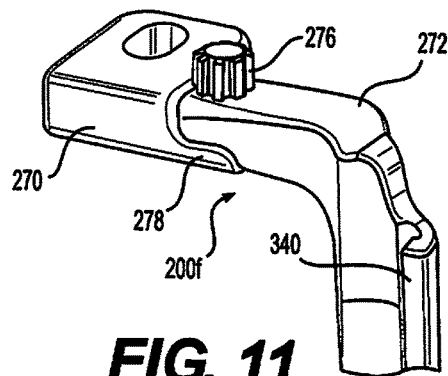
FIG. 11 depicts a blade mounting configuration of the disclosure.
Figure 12:
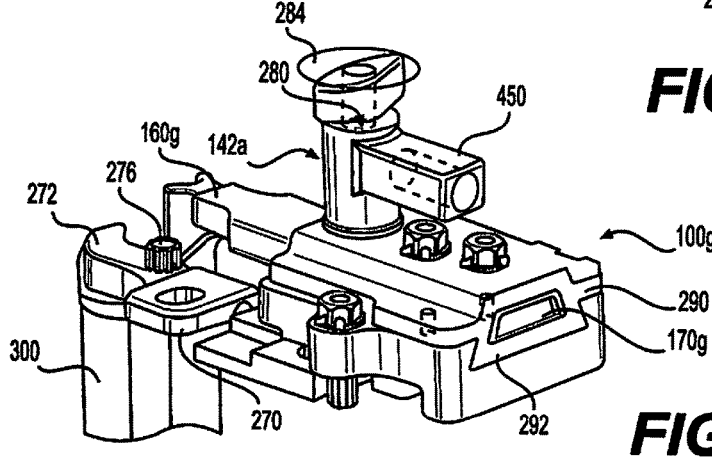
FIG. 12 depicts the blade mounting configuration of FIG. 11, connected to a retractor of the disclosure, the retractor configured with an alternative frame mount of the disclosure.

With reference to FIGS. 11-12, a compact blade holder 200F includes a mounting block 270 extending from or affixable to a remainder of retractor 10 using any known method. Block 270 includes a chamber 274 sized to receive a mounting holder extension 272. A set screw 276 is threadably retained within holder extension 272, and bears against a block flange 278 when extension 272 is inserted within chamber 274 and set screw 276 is tightened. Alternatively, set screw 276 can be threaded into block flange 278. In this manner, mounting holder extension 272 is releasably securable within block 270, and is thereby attachable to retainer 10. A blade engagement profile 240 extends from holder extension 272, and is connectable to a blade 300 as described with respect to FIGS. 1-2. In an alternative embodiment, blade 300 forms holder extension 272, and therefore is directly attachable to block 270 as described above.

Referring now to FIG. 12, frame mount 142A includes a central bore 280 through which a threaded screw 282 (not shown) can be passed, to threadably engage frame 100. In this manner, frame mount 142A can be rotated about an axis defined by bore 280 to a desired orientation. In this embodiment, a key 284 is connected to screw 282, and can be rotated to tighten screw 282 and thereby affix a position of frame mount 142A relative to frame 100.

In the embodiment of FIG. 12, screw 282 threadably engages a slideable block that is retained within frame 100G with a dovetail connection 292, and is thereby longitudinally positionable within frame 100. Extension 170G of arm 160G is slideably retained within slideable block 290, and may be adjusted within block 290 using any of the methods disclosed elsewhere herein, including a rack and pinion configuration. In the embodiment shown, pinch bolts 294 can be rotated to tighten or loosen extension 170G.

Figure 13:
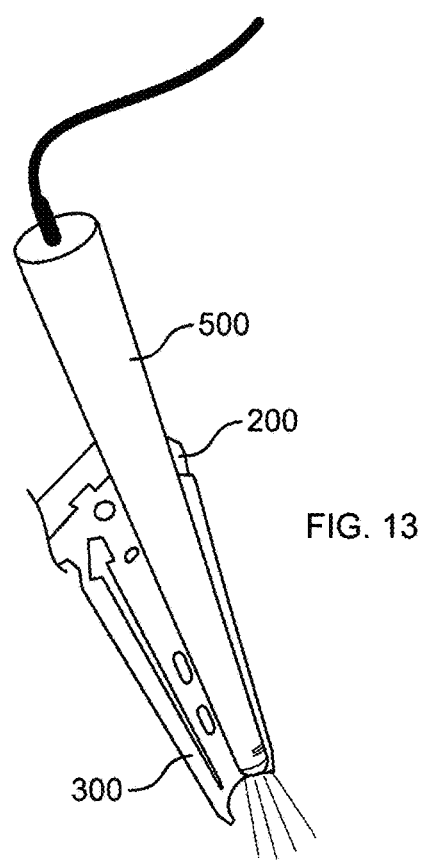
FIG. 13 depicts a light source retained by a blade holder of the disclosure.

Referring now to FIG. 13, a light source 500 can be affixed to blade 300, or to blade holder 200. Light source 500 can be provided with a blade holder profile 340 mateable with a blade engagement profile 240 of blade holder 200. Alternatively, light source 500 can be affixed to blade holder 200 or blade 300 using any known means, including for example magnetic, hook and loop fastener, threadable faster, resilient attachment means, or adhesive. A target of focus of light emitted from light source 500 can be adjusted by changing a pitch of blade holder 200, or by translating an associated arm 120, 140, 160, as needed.

Figure 14:
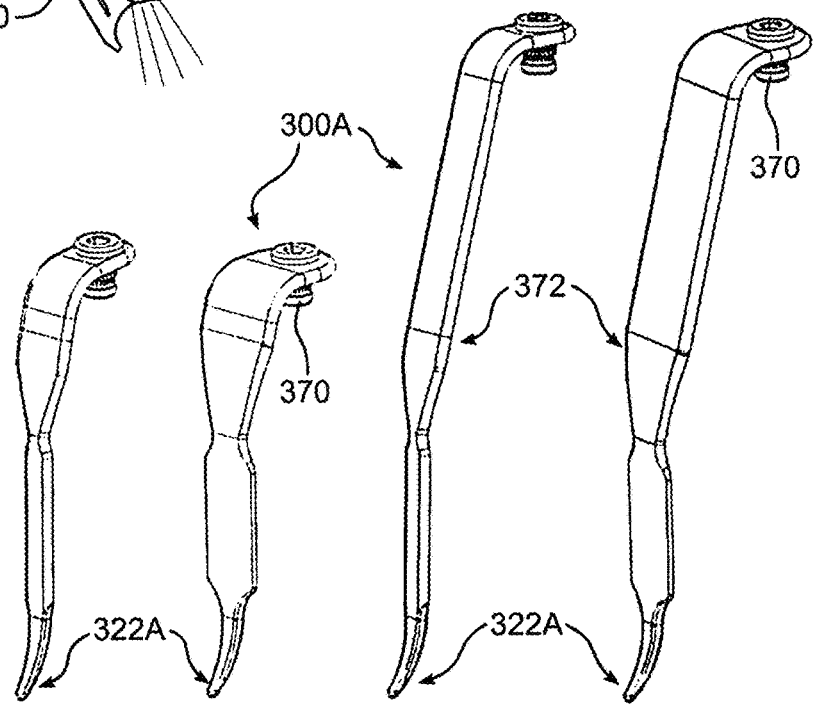
FIG. 14 depicts an alternative blade type, and an alternative blade mounting configuration, of the disclosure.

With reference to FIG. 14, a variety of blade shapes 300 can be employed together with retractor 10 of the disclosure. In addition, while blades 300 can be provided with a blade holder profile, as illustrated in FIGS. 1-2, blades 300 can alternatively be configured with a splined shaft 370, which can be mateable with a corresponding receiver provided upon blade holder 200 to secure retain blade 300, and to prevent rotation. In this manner, a wide variety of blade 300 styles and blade attachment mechanisms may be employed together with the various embodiments of the disclosure. In FIG. 14, blades 300A are configured to engage bone of the body, for example vertebrae. Blades 300A include are angled at 372 to enable mounting blocks 200 to be positioned further from the target surgical zone, and are further provided with tapered ends 322A which securely engage and retain bone. Accordingly, blades 300A do not form a tube 320 in this embodiment. It may also be seen that blades 300/300A can be provided in various lengths, widths, and if tubes 320 are formed, various lengths and diameter tubes. Blades 300/300A can be provided in a variety of sizes, including for example 8 mm to 18 mm wide, and lengths from 110 mm to 200 mm, although substantially narrower, wider, shorter, or longer blades can be provided. Although two blade types are illustrated herein, a wide variety of blade types, styles, sizes and lengths can be used in accordance with the disclosure.

Figure 17:
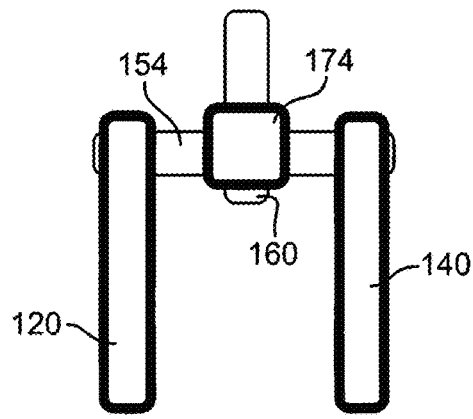
FIG. 17 is a diagram of the operative configuration of the retractor of FIGS. 1-2, in an open configuration.
Figure 18:
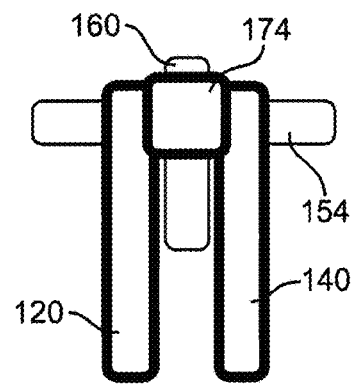
FIG. 18 depicts the retractor of FIG. 17, in a closed configuration.
Figure 19:
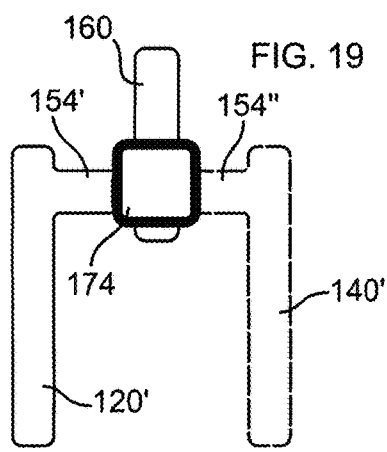
FIG. 19 is a diagram of an alternative retractor of the disclosure, in an open configuration.
Figure 20:
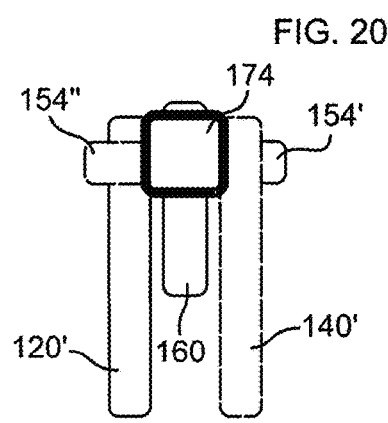
FIG. 20 depicts the retractor of FIG. 19, in a closed configuration.
Figure 21:
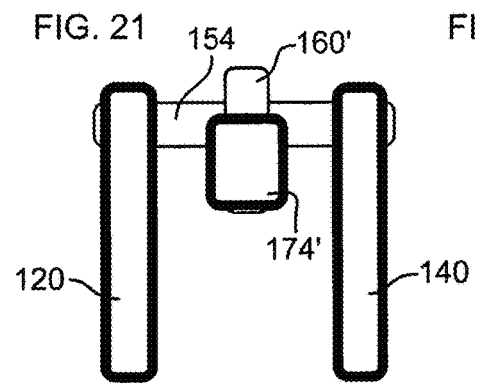
FIG. 21 is a diagram of another alternative retractor of the disclosure, in an open configuration.
Figure 22:
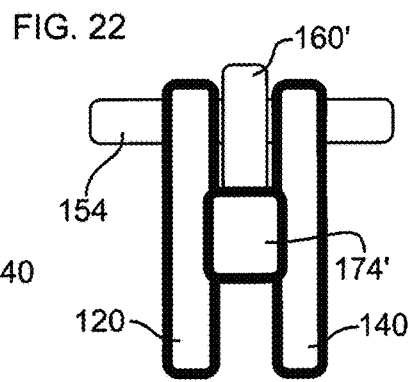
FIG. 22 depicts the retractor of FIG. 21 in a closed configuration.

FIGS. 17-22 diagrammatically illustrate three possible embodiments for carrying out the disclosure, wherein heavy outline represents a block into which an extension is slideable. In FIGS. 17-18, the embodiment of FIGS. 1-2 is depicted, wherein block 174 is affixed to extension 154, thereby forming a fixed core. The remaining components, arms 120, 140, and 160, are slideable independently of each other upon and within the core. In FIGS. 19-20, extensions 154' and 154" extend from arms 120' and 140'. Extensions 154', 154", and 160 slide at different height offsets within block 174, which alone forms the core within which the moveable arms slide. In FIGS. 21-22, arms 120 and 140 form blocks, as in FIGS. 17-18, and arm 160 is formed as a block 174', slideable upon extension 160', which is affixed to extension 154, extensions 160' and 154 forming a core upon which the moveable arms slide. It should be understood that only a single arm 120 or 140 can be provided, or that multiple arms 120 or 140, or multiple arms 160 can be provided, as benefit the therapeutic needs of the patient.

Frame 100 and its constituent components (including variants 100A-100H) may be fabricated from any one or more, or combinations of, metals, polymers, carbon fiber or other composites, natural materials, or any other materials having sufficient strength, durability, and biocompatibility. Materials selected can be radiolucent or radiopaque, as desired.

In accordance with the disclosure, a single mounting location for a frame 100 of the disclosure enables a posterior blade (e.g. 316) to be indexed without moving the cranial caudal blades (e.g. 312, 314), as well as allowing the cranial caudal blades to be indexed without moving the posterior blade.

All references cited herein are expressly incorporated by reference in their entirety. It will be appreciated by persons skilled in the art that the present invention is not limited to what has been particularly shown and described herein above. In addition, unless mention was made above to the contrary, it should be noted that all of the accompanying drawings are not to scale. There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

We claim:

1. A surgical retractor for retracting body tissue, comprising: a first arm defining proximal and distal ends and a first arm longitudinal axis extending therebetween, the distal end of the first arm comprising a first blade holder pivotally supporting a first retractor blade, the proximal end of the first arm forming a block having an aperture; a second arm defining proximal and distal ends and a second arm longitudinal axis extending therebetween, the distal end of the second arm comprising a second blade holder pivotally supporting a second retractor blade, the proximal end of the second arm forming a block having an aperture; a third arm defining proximal and distal ends and a third arm longitudinal axis extending therebetween, the distal end of the third arm comprising a third blade holder pivotally supporting a third retractor blade, the proximal end of the third arm forming a block disposed in between the block of the first arm and the block of the second arm, and a first rack having a first end portion and a second end portion, wherein the block of the first arm extends over the first end portion and the block of the second arm extends over the second end portion, wherein the first arm is slidable relative to the first rack and the second arm is slidable relative to the first rack; a second rack formed on a side surface of the third arm that intersects the first rack, wherein the first rack is a single member, wherein the first arm longitudinal axis, the second arm longitudinal axis, and the third arm longitudinal axis are generally parallel; and wherein a first threaded shaft is threadably received within the first arm, a second threaded shaft is threadably received within the second arm, and a third threaded shaft is threadably received within the third arm, the first, second, and third retractor blades being configured to pivot by rotation of the first, second, and third threaded shafts, respectively.

2. The retractor of claim 1, wherein the first arm further comprises a blade pitch tool engagement feature.

3. The retractor of claim 2, wherein the blade pitch tool engagement feature of the first arm is positioned proximally and away from the blade holder of the first arm.

4. The retractor of claim 1, wherein the blade holder of the first arm is pivotally mounted to the first arm and the blade holder of the second arm is pivotally mounted to the second arm.

5. The retractor of claim 1, wherein a light source is affixable to at least one of the first, second, or third retractor blades.

6. The retractor of claim 1, wherein the first arm and the second arm each comprise a pinion for engaging the first rack.

7. The retractor of claim 6, wherein the first arm comprises a first blade pitch tool engagement feature and the second arm comprises a second blade pitch tool engagement feature.

8. The retractor of claim 7, wherein first the blade pitch tool engagement feature of the first arm adjusts a pitch of the first retractor blade and the second blade pitch tool engagement feature of the second arm adjusts a pitch of the second retractor blade.

9. The retractor of claim 8, wherein the pitch of the first retractor blade is independently adjustable from the pitch of the second retractor blade.

10. A surgical retractor for retracting body tissue, comprising: a first arm defining proximal and distal ends and a first arm longitudinal axis extending therebetween, the proximal end of the first arm defining a first block having a first aperture, the first aperture defining a first aperture longitudinal axis that is transverse to the first arm longitudinal axis, the distal end of the first arm comprising a first blade holder pivotally supporting a first retractor blade; a second arm defining proximal and distal ends and a second arm longitudinal axis extending therebetween, the proximal end of the second arm defining a second block having a second aperture, the second aperture defining a second aperture longitudinal axis that is transverse to the second arm longitudinal axis, the distal end of the second arm comprising a second blade holder pivotally supporting a second retractor blade; a third arm defining proximal and distal ends and a third arm longitudinal axis extending therebetween, the distal end of the third arm comprising a third blade holder pivotally supporting a third retractor blade, the proximal end of the third arm forming a block disposed in between the block of the first arm and the block of the second arm; and a first rack having a first end portion and a second end portion, wherein the block of the first arm extends over the first end portion and the block of the second arm extends over the second end portion, wherein the first arm is slidable relative to the first rack and the second arm is slidable relative to the first rack; a second toothed rack formed on a side surface of the third arm that intersects the first rack, wherein the first rack is a single member, wherein the first arm longitudinal axis, the second arm longitudinal axis, and the third arm longitudinal axis are generally parallel; and wherein a first threaded shaft is threadably received within the first arm, a second threaded shaft is threadably received within the second arm, and a third threaded shaft is threadably received within the third arm, the first, second, and third retractor blades being configured to pivot by rotation of the first, second, and third threaded shafts, respectively.

* * * * *